United States Patent [19]

Kaiser et al.

[11] 4,107,299
[45] Aug. 15, 1978

[54] CARDIOACTIVE 12-EPI-DIGOXIN AND DERIVATIVES THEREOF

[75] Inventors: Fritz Kaiser, Lampertheim; Wolfgang Schaumann, Heidelberg, both of Germany; Kurt Stach, deceased, late of Mannheim-Waldhof, Germany; by Werner Plattner, administrator, Linz, Austria; Wolfgang Voigtländer, Viernheim, Germany

[73] Assignee: Boehringer Mannheim GmbH, Mannheim-Waldhof, Fed. Rep. of Germany

[21] Appl. No.: 738,808

[22] Filed: Nov. 4, 1976

[30] Foreign Application Priority Data

Nov. 10, 1975 [DE] Fed. Rep. of Germany ....... 2550354

[51] Int. Cl.² .................. A61K 31/705; C07J 19/00
[52] U.S. Cl. ........................................ 424/182; 536/7
[58] Field of Search ................ 424/182; 536/7, 5

[56] References Cited

U.S. PATENT DOCUMENTS

| | | | |
|---|---|---|---|
| 3,538,078 | 11/1970 | Kaiser et al. ................... | 536/7 |
| 3,696,091 | 10/1972 | Eberlein et al. ................. | 536/7 |
| 3,909,357 | 9/1975 | Reinhard et al. ................ | 536/7 |
| 3,937,697 | 2/1976 | Stache et al. ................... | 536/7 |
| 3,963,697 | 6/1976 | Coombes ......................... | 536/7 |
| 3,981,862 | 9/1976 | Voigtlander et al. ........... | 536/7 |

*Primary Examiner*—Johnnie R. Brown

*Attorney, Agent, or Firm*—Burgess, Dinklage & Sprung

[57] ABSTRACT

12-Epi-digoxins of the formula

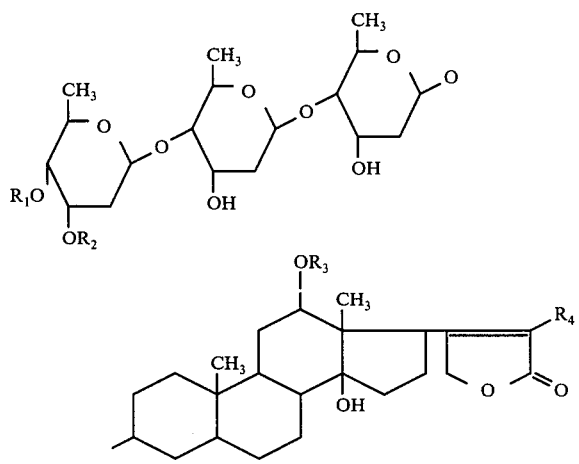

wherein
$R_1$ and $R_2$ each independently is hydrogen or a lower alkanoyl or alkyl radical,
$R_3$ is hydrogen or a lower alkanoyl radical, and
$R_4$ is hydrogen or a lower alkyl, alkenyl or alkynyl radical, are characterized by marked cardioactivity and therapeutic spectrum. They are produced by reduction of the corresponding 12-dehydrodigoxin.

9 Claims, No Drawings

CARDIOACTIVE 12-EPI-DIGOXIN AND DERIVATIVES THEREOF

The present invention is concerned with 12-epi-digoxin and the derivatives thereof and with the preparation of these new compounds.

12-Epi-digoxin and the derivatives thereof according to the present invention can be represented by the general formula:

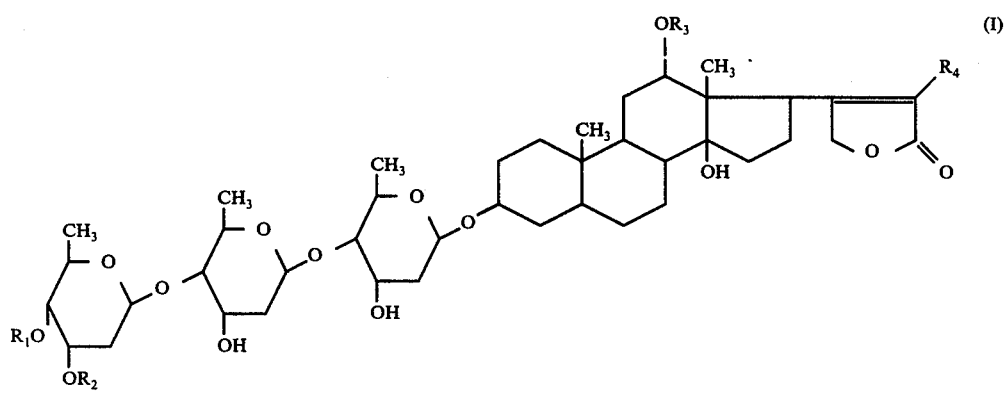

wherein $R_1$ and $R_2$, which can be the same or different, are hydrogen atoms or acyl or lower alkyl radicals, $R_3$ is a hydrogen atom or an acyl radical and $R_4$ is a hydrogen atom or a saturated or unsatured, branched or unbranched aliphatic hydrocarbon radical containing up to 4 carbon atoms.

The acyl radicals represented by the symbols $R_1$, $R_2$ and $R_3$ can contain up to 4 carbon atoms, the acetyl radical being preferred.

The lower alkyl radicals represented by the symbols $R_1$ and $R_2$ can contain up to 4 carbon atoms, the methyl and ethyl radicals being preferred.

We have found that the new digoxin derivatives according to the present invention have a substantially better therapeutic spectrum than the corresponding known digoxin derivatives. Therefore, they are especially well-suited for the therapy of cardiac insufficiency.

The new compounds according to the present invention can be prepared by the hydrogenation of compounds of the general formala:

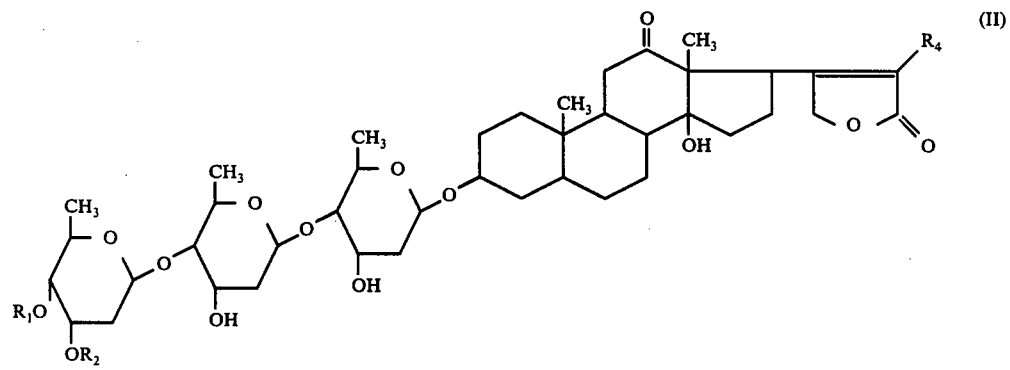

wherein $R_1$, $R_2$ and $R_4$ have the same meanings as above, whereafter the substituents $R_1$, $R_2$, $R_3$ and $R_4$ in the product obtained are, if desired, converted into different substituents having the above-given meanings.

12-Dehydrodigoxin derivatives used as starting materials are known compounds, the preparation of which is described in the literature (see A. V. Wartburg et al., Biochem. Pharmacol., 14, 1883/1965; and German Pat. No. 2,410,012), for example, the corresponding digoxin derivative is oxidized to the 12-dehydrodigoxin compound.

The reduction of the 12-dehydrodigoxin derivatives can be carried out by hydrogenation with metal hydrides, preferably lithium tri-tert.-butoxy-aluminum hydride, in anhydrous tetrahydrofuran.

The conversion of the substituents after the reduction has taken place can be carried out in the usual manner. Thus, the selective introduction of alkyl radicals $R_1$ and $R_2$ can be carried out by the process described in German Pat. No. 1,961,034. The introduction of acetyl radicals $R_1$, $R_2$ and $R_3$ can be carried out by the process described in Arzneimittelforschung, 15, 481/1965 and in German Pat. Nos. 2,206,737 and 2,126,305, whereas, for example, the introduction of the C 22 alkyl radical $R_4$ can be carried out in the manner described in German Pat. Nos. 2,418,127; 2,457,219 and 2,433,563.

The new compounds obtained of general formula (I) can be isolated by multiplicative partitioning and subsequently recrystallized.

The new compounds (I) according to the present invention can be administered enterally or parenterally in liquid or solid form. Thus, the present invention also provides pharmaceutical compositions comprising at least one of the new compounds (I) in admixture with a solid or liquid pharmaceutical diluent or carrier. As injection medium, it is preferred to use water which contains the additives usual in the case of injection solutions, such as stabilizing agents, solubilizing agents and buffers. Additives of this type include, for example, tartrate and citrate buffers, ethanol, complex-forming agents (such as ethylenediamine-tetraacetic acid and the non-toxic salts thereof), and high molecular weight polymers (such as liquid polyethylene oxide) for viscosity regulation. Solid carrier materials include, for example, starch, lactose, mannitol, methyl cellulose, talc, highly-dispersed silicic acid, high molecular weight fatty acids (such as stearic acid), gelatine, agar-agar, calcium phosphate, magnesium stearate, animal and vegetable fats and solid high molecular weight polymers (such as polyethylene glycols); compositions suitable for oral administration can, if desired, contain flavoring and sweetening agents.

For making tablets, pills and other solid forms for medication, uniform dispersion of the active compound throughout the carrier is required. Such a fine and uniform dispersion is achieved for instance by intimately mixing and milling the 12-epi-dixogins according to the present invention with a solid pulverulent diluent and, if required, with tableting adjuvants to the desired degree of fineness. One may also impregnate the finely pulverized, solid carrier, while milling, with a solution of the active compound in water or a suitable solvent and remove the solvent during such milling.

As solid pharmaceutical carriers, various inert pulverulent distributing agents, as they are conventionally used in the pharmaceutical industry, may be employed.

Solid diluents which are admixed with the active compounds, especially when preparing tablets, pills and other compressed forms, are the commonly used diluting agents, such as cornstarch, dextrose, lactose, sugar and the like. For making tablets and other compressed medication forms, binders such as pectins, gelatin, gum arabic, methylcellulose, yeast extract, agar, tragacanth, and lubricants such as magnesium stearate, calcium stearate, stearic acid, talc and the like are used.

The amount of 12-epi-digoxins present in such preparations may, of course, vary. It is necessary that the active ingredients be contained therein in such an amount that a suitable dosage will be ensured. Ordinarily the preparations should not contain less than about 0.1 mg of the active 12-epi-digoxins. The preferred amount in orally administered preparations such as tablets, pills and the like, is between about 0.2 mg and 1.0 mg per day.

The doses to be administered vary according to the type of action desired, i.e. whether said action is to be digitalization or maintenance. It is, of course, understood that the physician will determine the proper amounts to be given to a patient depending upon the symptoms to be alleviated and the patient's condition and that the doses given above are by no means limiting the new digoxin ethers to such dosages.

The following Examples are given for the purpose of illustrating the present invention:

EXAMPLE 1

12-Epi-digoxin 10 g. 12-dehydrodigoxin, dissolved in 700 ml. anhydrous tetrahydrofuran, are, after the addition of 23 g. lithium tri-tert.-butoxy-aluminum hydride, stirred for 20 hours at ambient temperature. After the addition of 180 ml. 20% aqueous acetic acid and 550 ml. water, the reaction mixture is shaken out with chloroform and the chloroform phases are washed twice with 5% aqueous sodium bicarbonate solution and with water. After drying over anhydrous sodium sulphate, the solution is filtered and the filtrate is evaporated in a vacuum. The crude product obtained, which is a mixture of 12-epi-digoxin and digoxin, is separated by multiplicative partitioning with the phase mixture carbon tetrachloride-ethyl acetate-methanol-water (3:3:2:4 v/v). From the evaporated organic phase there are obtained, after crystallization from cloroform-methanol-diethyl ether, 5.6 g. 12-epi-digoxin; m.p. 211°–215° C.

EXAMPLE 2

12-Epi-$\beta$-methyldigoxin 10 g. 12-dehydro-$\beta$-methyldigoxin, dissolved in 700 ml. anhydrous tetrahydrofuran, are, after the addition of 23 g. lithium tri-tert.-butoxy-aluminum hydride, reacted in the manner described in Example 1 and worked up. The crude product obtained is subjected to multiplicative partitioning with the phase mixture carbon tetrachloride-ethyl acetate-methanol-water (4:2:3:3 v/v). The evaporated organic phases yield, after crystallization from chloroform-methanol-diethyl ether, 5.4 g. 12-epi-$\beta$-methyldigoxin; m.p. 221°–225° C.

EXAMPLE 3

12-Epi-$\beta$-methyldigoxin 2 g. 12-epi-digoxin are dissolved in 15 ml. dimethyl formamide and mixed with 15 ml. toluene, 2.46 g. strontium hydroxide and 1.54 g. aluminum oxide (Merck, according to Brockmann). 4.62 ml. dimethyl sulphate in 25 ml. toluene are added at ambient temperature, while stirring. Subsequently, the reaction mixture is stirred for 4 hours at ambient temperature, then diluted with 100 ml. chloroform, filtered with suction through kieselguhr, washed with chloroform, mixed with 24 ml. pyridine and evaporated in a vacuum down to a very viscous residue. This is taken up in 60 ml. chloroform and shaken out three times with 10 ml. amounts of water. The collected wash water is again shaken out once with 10 ml. chloroform and the combined chloroform phases, after drying over anhydrous sodium sulphate and filtering, are evaporated in a vacuum. The dry residue is subjected to multiplicative partitioning with the phase mixture carbon tetrachloride-ethyl acetate-methanol-water (4:2:3:3 v/v). From the organic phase there is obtained, after evaporation in a vacuum and crystallization of the residue from chloroform-methanol-diethyl ether, 1.1 g. 12-epi-$\beta$-methyldigoxin; m.p. 220°–224° C.

EXAMPLE 4

12-Epi-$\beta$-methyldigoxin 5 g. 12-dehydro-$\alpha$-methyldigoxin, dissolved in 350 ml. anhydrous tetrahydrofuran, are, after the addition of 11.5 g. lithium tri-tert.-butoxy-aluminum, hydride, reacted in the manner described in Example 1 and worked up. The crude product obtained is subjected to multiplicative partitioning with the phase mixture carbon tetrachlorideethyl acetate-methanol-water (4:2:3:3 v/v). The evaporated organic phases yield, after evaporation and crystallization of the residue from chloroform-methanol-diethyl ether, 2.1 g. 12-epi-$\alpha$-methyldigoxin; m.p. 163°–167° C.

EXAMPLE 5

$\alpha$-Acetyl-12-epi-digoxin 8.9 g. dimethyl acetamide and 12.6 g. dimethyl sulphate are stirred for 2 hours at 80° C. and, after cooling, mixed with 100 ml. chloroform and 8.2 g. anhydrous sodium acetate and stirred overnight at ambient temperature. Subseqently, 2 g. 12-epi-digoxin are added thereto and the reaction mixture is stirred for 3 hours at ambient temperature. The reaction mixture is then mixed with 40 ml. 50% formic acid and further stirred for 2 hours at ambient temperature. The organic phase, after the addition of 100 ml. chloroform, is washed with 5% aqueous sodium bicarbonate solution and water, dried over anhydrous sodium sulphate and evaporated in a vacuum. The crude product obtained is separated with cyclohexane-ethyl acetate (1:1 v/v) over a column of cellulose (impregnated with formamide). The chromatographically uniform fractions are evaporated and the residue is crystallized from chloroform-methanol-diethyl ether to give 580 mg. α-acetyl-12-epi-digoxin; m.p. 206°–211° C.

EXAMPLE 6

β-Acetyl-12-epi-digoxin 1.2 g. 12-epi-digoxin, dissolved in 12 ml. dimethyl formamide, are mixed with 240 mg. triethylenediamine and 240 mg. acetic anhydride and left to stand for 24 hours at ambient temperature. After dilution of the reaction mixture with 180 ml. water, the precipitate obtained is filtered off, dried and fractioned with cyclohexane-ethyl acetate (1:1 v/v) over a column of cellulose (impregnated with formamide). The chromatographically uniform fractions yield, after evaporation and crystallization of the residue from methanol-water (1:1 v/v), 520 mg. β-acetyl-12-epi-digoxin; m.p. 278°–281° C.

EXAMPLE 7

12-Acetyl-12-epi-digoxin 2 g. 12-epi-digoxin, dissolved in 10 ml. pyridine, are mixed with 920 mg. acetic anhydride and heated to 40° C. for 5 hours. Subsequently, the reaction mixture is diluted with water, shaken out with chloroform and the chloroform phase is washed with 2N sulphuric acid, aqueous sodium carbonate solution and water, evaporated in a vacuum and the crude product dissolved in 200 ml. methanol, mixed with 1.9 g. potassium bicarbonate and 100 mg. potassium carbonate in 100 ml. water and heated for 5 hours at 40° C. After diluting the reaction mixture with water and shaking out with chloroform, the chloroform phase is evaporated and the residue obtained is separated with xylene-methyl ethyl ketone (3:2 v/v) over a column of cellulose (impregnated with formamide). The chromatographically uniform fractions yield, after evaporation and crystallization of the residue from chloroform-methanol-diethyl ether, 410 mg. 12-acetyl-12-epi-digoxin; m.p. 158°–163° C.

EXAMPLE 8

22-Methyl-12-epi-digoxin 1.5 g. 12-epi-digoxin, dissolved in 15 ml. dimethyl sulphoxide, are mixed with 1.05 ml. methyl iodide. 210 mg. sodium hydride (50% suspension in oil) are added portionwise within the course of 10 minutes, while stirring at ambient temperature. The reaction mixture is stirred for a further 10 minutes, diluted with 100 ml. chloroform, filtered over aluminum oxide, subsequently washed with chloroform-methanol (1:1 v/v) and the filtrate evaporated in a vacuum. The crude product obtained is separated with xylene-methyl ethyl ketone (2:1 v/v) over a column of cellulose (impregnated with formamide). The chromatographically uniform fractions, after evaporation and recrystallization of the residue from chloroform-methanol-diethyl etherpetroleum ether, give 360 mg. 22-methyl-12-epi-digoxin; m.p. 166°–170° C.

EXAMPLE 9

22-Ethyl-12-epi-digoxin 2.4 g. 12-epi-digoxin, dissolved in 24 ml. dimethyl sulphoxide, are reacted with 1.7 ml. ethyl iodide and 336 mg. sodium hydride (50% suspension in oil) in the manner described in Example 8 and worked up. The crude product obtained is separated with xylene-methyl ethyl ketone (2:1 v/v) over a column of cellulose (impregnated with formamide). The chromatographically uniform fractions, after evaporation and crystallization to the residue from chloroform methanol-diethyl ether, give 620 mg. 22-ethyl-12-epi-digoxin; m.p. 183°–188° C.

EXAMPLE 10

22-n-Butyl-12-epi-digoxin 1.6 g. 12-epi-digoxin, dissolved in 16 ml. dimethyl sulphoxide, are reacted in the manner described in Example 8 with 1.36 ml. n-butyl iodide and 192 mg. sodium hydride (50% suspension in oil) and worked up. The chromatographically uniform fractions yield, after evaporation and crystallization of the residue from chloroform methanol-diethyl ether-petroleum ether, 580 mg. 22-n-butyl-12-epi-digoxin; m.p. 156°–160° C.

EXAMPLE 11

22-Ethyl-12-epi-α-methyldigoxin 1 g. 12-epi-α-methyldigoxin, dissolved in 10 ml. dimethyl sulphoxide, is reacted in the manner described in Example 8 with 0.7 ml. ethyl iodide and 136 mg. sodium hydride (50% suspension in oil) and worked up. The crude product obtained is separated with cyclohexane-ethyl acetate (2:1 v/v) over a column of cellulose (impregnated with formamide). The chromatographically uniform fractions, after evaporation and crystallization of the residue from chloroform-methanol-diethyl ether, give 320 mg. 22-ethyl-12-epi-α-methyldigoxin; m.p. 151°–155° C.

EXAMPLE 12

22-Methyl-12-epi-β-methyldigoxin 1.6 g. 12-epi-β-methyldigoxin, dissolved in 16 ml. dimethyl formamide, are reacted in the manner described in Example 8 with 0.56 ml. methyl iodide and 168 mg. sodium hydride (50% suspension in oil) and worked up. The crude product obtained is separated with cyclohexane-ethyl acetate (2:1 v/v) over a column of cellulose (impregnated with formamide). The chromatographically uniform fractions, after evaporation and crystallization of the residue from chloroform-methanol-diethyl ether-petroleum ether, give 480 mg. 22-methyl-12-epi-β-methyldigoxin; m.p. 161°–165° C.

EXAMPLE 13

22-Ethyl-12-epi-β-methyldigoxin 2.4 g. 12-epi-β-methyldigoxin, dissolved in 24 ml. dimethyl sulphoxide, are reacted in the manner described in Example 8 with 1.7 ml. ethyl iodide and 336 mg. sodium hydride (50% suspension in oil) and worked up. The crude product obtained is separated with xylene-methyl ethyl ketone (3:1 v/v) over a column of cellulose (impregnated with formamide). The chromatographically uniform fractions, after evaporation and crystallization of the residue from chloroform-methanol-diethyl ether, give 680 mg. 22-ethyl-12-epi-β-methyldigoxin; m.p. 264°–269° C.

EXAMPLE 14

22-Isopropyl-12-epi-β-methyldigoxin.

1.6 g. 12-epi-β-methyldigoxin, dissolved in 16 ml. dimethyl formamide, are reacted in the manner described in Example 8 with 1.2 ml. isopropyl iodide and 192 mg. sodium hydride (50% suspension in oil) and worked up. The crude product obtained is separated with cyclohexaneethyl acetate (2:1 v/v) over a column of cellulose (impregnated with formamide). The chromatographically uniform fractions, after evaporation and crystallization of the residue from chloroform-methanol-diethyl ether-petroleum ether, give 320 mg. 22-isopropyl-12-epi-β-methyldigoxin; m.p. 156°–160° C.

EXAMPLE 15

22-Allyl-12-epi-β-methyldigoxin 1.6 g. 12-epi-β-methyldigoxin, dissolved in 16 ml. dimethyl formamide, are reacted in the manner described in Example 8 with 2.0 ml. allyl bromide and 168 mg. sodium hydride (50% suspension in oil) and worked up. The crude product obtained is separated with cyclohexane-ethyl acetate (2:1 v/v) over a column of cellulose (impregnated with formamide). The chromatographically uniform fractions, after evaporation and crystallization of the residue from chloroform-methanol-diethyl ether-petroleum ether, give 360 mg. 22-allyl-12-epi-β-methyldigoxin; m.p. 146°–151° C.

EXAMPLE 16

12-Epi-β-ethyldigoxin 5 g. 12-dehydro-β-ethyldigoxin in 350 ml. anhydrous tetrahydrofuran are, after the addition of 11.5 g. lithium tri-tert.-butoxy-aluminum hydride, reacted in the manner described in Example 1 and worked up. The crude product obtained is separated with cyclohexane-ethyl acetate (2:1 v/v) over a column of cellulose (impregnated with formamide). The chromatographically uniform fractions, after evaporation and crystallization of the residue from chloroform-diethyl ether, give 2.2 g. 12-epi-β-ethyldigoxin; m.p. 156°–160° C.

EXAMPLE 17

12-Epi-α,β-dimethyldigoxin 2.5 g. 12-dehydro-α,β-dimethyldigoxin, dissolved in 175 ml. anydrous tetrahydrofuran, are, after the addition of 6 g. lithium tri-tert.-butoxy-aluminum hydride, reacted in the manner described in Example 1 and worked up. The crude product is separated with cyclohexane-ethyl acetate (2:1 v/v) over a column of cellulose (impregnated with formamide). The chromatographically uniform fractions, after evaporation and crystallization of the residue from chloroform-diethyl ether, give 1.3 g. 12-epi-α,β-dimethyldigoxin; m.p. 235°–228° C.

EXAMPLE 18

12-Acetyl-12-epi-β-methyldigoxin.

3 g. 12-epi-β-methyldigoxin, dissolved in 15 ml. pyridine, are, after the addition of 1.4 g. acetic anhydride, left to stand for 5 hours at ambient temperature. The reaction mixture is subsequently diluted with water, shaken out with chloroform, washed with water, dried over anhydrous sodium sulphate, filtered and the filtrate evaporated in a vacuum. The crude product is separated with cyclohexane-ethyl acetate (2:1 v/v) over a column of cellulose (impregnated with formamide). The chromatographically uniform fractions, after evaporation and crystallization of the residue from chloroform-diethyl ether-petroleum ether, give 450 mg. 12-acetyl-12-epi-β-methyldigoxin; m.p. 224°–226° C.

EXAMPLE 19

22-Isopropyl-12-epi-digoxin 1.6 g. 12-epi-digoxin, dissolved in 16 ml. dimethyl sulphoxide, are reacted in the manner described in Example 8 with 1.2 ml. isopropyl iodide and 192 mg. sodium hydride (50% suspension in oil) and worked up. The crude product obtained is separated with xylene-methyl ethyl ketone (2:1 v/v) over a column of cellulose (impregnated with formamide). The chromatographically uniform fractions, after evaporation and crystallization of the residue from chloroform-methanol-diethyl ether, give 350 mg. 22-isopropyl-12-epi-digoxin; m.p. 166;20 –170° C.

EXAMPLE 20

22-n-Butyl-12-epi-β-methyldigoxin 2 g. 12-epi-β-methyldigoxin, dissolved in 20 ml. dimethyl formamide, are reacted in the manner described in Example 8 with 1.7 ml. n-butyl iodide and 240 mg. sodium hydride (50% suspension in oil) and worked up. The crude product obtained is separated with cyclohexane-ethyl acetate (3:1 v/v) over a column of cellulose (impregnated with formamide). The chromatographically uniform fractions, after evaporation and crystallization of the residue from chloroform-methanol-diethyl ether, give 550 mg. 22-n-butyl-12-epi-β-methyldigoxin; m.p. 143°–147° C.

EXAMPLE 21

22-Allyl-12-epi-digoxin 2 g. 12-epi-digoxin, dissolved in 20 ml. dimethyl formamide, are reacted with 3.5 ml. allyl bromide and 140 mg. sodium hydride (50% suspension in oil) in the manner described in Example 8 and the reaction mixture then worked up. The crude product is separated with xylene-methyl ethyl ketone (2:1 v/v) over a column of cellulose (impregnated with formamide). The chromatographically uniform fractions, after evaporation and crystallization of the residue from chloroform-methanol-diethyl ether, give 450 mg. 22-allyl-12-epi-digoxin; m.p. 158°–163° C.

EXAMPLE 22

α,β-Diacetyl-12-epi-digoxin 3 g. 12-epi-digoxin, dissolved in 30 ml. dimethyl formamide, are, after the addition of 600 mg. triethylamine and 420 mg. acetic anhydride, left to stand for 24 hours at ambient temperature. A further 0.4 ml. acetic anhydride are then added and the reaction mixture is again left to stand for 24 hours. After diluting the reaction mixture with 60 ml. water, the precipitate formed is filtered off with suction, dried and separated with cyclohexane-ethyl acetate (2:1 v/v) over a column of cellulose (impregnated with formamide). The chromatographically uniform fractions, after evaporation and crystallization of the residue from chloroform-diethyl ether-petroleum ether, give 590 mg. α,β-diacetyl-12-epi-digoxin; m.p. 206°–210° C.

EXAMPLE 23

12-Propionyl-12-epi-digoxin 3 g. 12-epi-digoxin, dissolved in 15 ml. pyridine, are, after the addition of 1.75 g. propionic anhydride, left to stand for 24 hours at ambient temperature. Subsequently, the reaction mixture is further worked up in a manner analogous to that described in Example 7. The crude product obtained is separated with cyclohexane-ethyl acetate (1:1 v/v) over a column of cellulose (impregnated with formamide). The chromatographically uniform fractions, after evaporation and crystallization of the residue from chloroform-methanol-diethyl ether, give 390 mg. 12-propionyl-12-epi-digoxin; m.p. 136°–140° C.

EXAMPLE 24

12-Propionyl-12-epi-β-methyldigoxin 2.5 g. 12-epi-β-methyldigoxin, dissolved in 25 ml. pyridine, are, after the addition of 12.5 ml. propionic anhydride, left to stand for 24 hours at ambient temperature. Subsequently, the reaction mixture is further worked up in the manner described in Example 7. The crude product is separated with cyclohexane-ethyl acetate (2:1 v/v) over a column of cellulose (impregnated with formamide). The chromatographically uniform fractions, after evaporation and crystallization of the residue from chloroform-diethyl ether-petroleum ether, give 330 mg. 12-propionyl-12-epi-β-methyldigoxin; m.p. 141°–145° C.

EXAMPLE 25

22-Propargyl-12-epi-digoxin 1.4 g. 12-epi-digoxin, dissolved in 14 ml. dimethyl fomamide, are reacted with 620 mg. 3-bromo-1-propyne and 84 mg. sodium hydride (50% suspension in oil) in the manner described in Example 8 and worked up. The crude product is separated with cyclohexane-ethyl acetate (2:3 v/v) over a column of cellulose (impregnated with formamide). The chromatographically uniform fractions, after evaporation and crystallization of the residue from chloroform-methanol-diethyl ether, give 350 mg. 22-propargyl-12-epi-digoxin: m.p. 149°–153° C.

EXAMPLE 26

22-Propargyl-12-epi-β-methyldigoxin 1.5 g. 12-epi-βmethyldigoxin, dissolved in 12 ml. dimethyl formamide, are reacted with 1.07 g. 3-bromo-1-propyne and 144 mg. sodium hydride (50% suspension in oil) in the manner described in Example 8 and then worked up. The crude product is separated with cyclohexane-ethyl acetate (2:1 v/v) over a column of cellulose (impregnated with formamide). The chromatographically uniform fractions, after evaporation and crystallization of the residue from chloroform-diethyl ether-petroleum ether, give 400 mg. 22-propargyl-12-epi-β-methyldigoxin; m.p. 185°–187° C.

Comparison of the therapeutic spectrum of various cardioactive glycosides was undertaken, employing electrical stimulation of the insulated left atrium of guinea pigs. Specifically, the left atrium was suspended in Tyrode solution at 31° C and electrically stimulated by a frequency of 3 Hz with rectangular impulses of 2 m sec. duration and optimum tension. The maximum contraction strength was registered semi-isometrically.

When a constant contraction amplitude has set in, the calcium concentration was reduced from 1.8 to 0.45 mVal. The initial tension was adjusted to 1 g at the start of the test; if necessary, it was adjusted after the readjustment to a solution poor in calcium, however, no longer changed during the further course of the experiment.

Of the glycosides to be tested, stock solutions were prepared in dimethyl acetamide and, for the test with NaCl-solution so diluted that the stated end concentrations were obtained with the addition of 0.1 ml to a bath volume of 80 ml. It was determined in preliminary tests that up to 0.4 ml undiluted dimethyl acetamide were tolerated without influencing the contractility.

If, after reduction of the calcium concnetration, a constant degree of contraction was again obtained after approximately 10 minutes, concentrations of the glycoside to be tested were added in the ratio 1 + 1 + 2 + 4, etc. The period between the individual additions was 15 minutes.

Prior to the change-over to a calcium-poor Tyrode solution and prior to each addition of glycoside, as well as 15 minutes after the last dose, the prestress was measured in grams and the contraction amplitude in mg. The difference of the amplitude was calculated from the test values for the contraction amplitude after reduction of the calcium content. The difference between the contraction amplitude before and after the change-over to a calcium-poor solution was put as equal to 100% amplitude reduction.

It was determined for each individual atrium when, with administration of increasing concentrations of the glycosides, there was obtained
the maximum contraction amplitude ("maximum increase");
increase of the amplitude to 50% of the difference between normal and reduced calcium content ("$EC_{50}$ increase");
decrease of the contraction amplitude to the same height ("$EC_{50}$ decrease");
the therapeutic spectrum quotient of the two $EC_{50}$, i.e. $EC_{50}$ decrease/$EC_{50}$ increase.

With these evaluation processes, there are obtained numerical data for the concentration and the period during which the corresponding effect was observed. In order to obtain a uniform basis for the evaluation, differences in the time of the appearance were converted into concentrations according to the following method:

The logarithm of the concentration was graphically plotted against the time in such manner that the lowest concentration was put at 15 minutes, the next higher one at 30 minutes, etc. The evaluation of the tests yielded the time after the start of the test at which the respective effect had appeared. The concentration pertaining to it was read from the diagram.

This procedure is based on the assumption that the concentration increases exponentially at the place of the effect. De facto this assumption is more correct than a regular increase in concentration in stages in the bath liquid since there is a substantial time lapse between the increase of the concentration in the bath and in the tissue.

In addition, the maximum degree of concentration was measured in all tests under the influence of the glycosides and in percentage of the decrease of the amplitude by reduction of the calcium content.

The results obtained are set out in the following Table which show consistent and markedly higher activities for the novel compounds with generally superior therapeutic spectra compared with β-methyldigoxin as control.

TABLE

Therapeutic effect and therapeutic spectrum at the insulated, electrically stimulated left atrium of the guinea pig.
Arithmetic means values and their average deviation.
S = concentration of the stock solution millimoles;
A = starting concentration after the first injection, micromoles;
N = number of guinea pigs tested.

| Active Material of Example of | S | A | N | Contraction Amplitude maximum increase | | | $EC_{50}$ in micromoles | | therapeutic spectrum |
|---|---|---|---|---|---|---|---|---|---|
| | | | | mg. | % | micromoles | increase | decrease | |
| Control -β-methyldigoxin | 3.2 | 0.125 | 5 | 292±56 | 75±5 | 0.37±0.03 | 0.23±0.03 | 0.66±0.04 | 3.06±0.36 |
| 1 | 1.92 | 0.25 | 5 | 746±56 | 92±6.5 | 1.22±0.20 | 0.557±0.07 | 2.48±0.30 | 4.49±0.35 |
| 2 & 3 | 1.92 | 0.125 | 5 | 666±78 | 96±6.3 | 1.057±0.17 | 0.315±0.02 | 2.78±0.40 | 8.86±1.17 |
| 5 | 3.84 | 0.5 | 6 | — | — | — | 0.848±0.09 | 2.78±0.28 | 3.40±0.40 |
| 6 | 1.92 | 0.5 | 6 | — | — | — | 0.921±0.07 | 3.76±0.25 | 4.25±0.51 |
| 7 | 3.84 | 1.0 | 6 | — | — | — | 2.86±0.31 | 13.8±0.81 | 5.15±0.71 |
| 9 | 3.84 | 1.0 | 6 | — | — | — | 6.63±0.75 | 39.3±3.0 | 6.39±0.96 |
| 12 | 3.84 | 1.0 | 8 | — | — | — | 3.55±0.41 | 17.0±1.7 | 5.15±0.59 |
| 13 | 3.84 | 1.4 | 6 | — | — | — | 5.90±0.48 | 40.5±2.6 | 7.10±0.74 |
| 14 | 3.84 | 2.0 | 7 | — | — | — | 21.6±1.9 | 61.9±5.2 | 3.08±0.45 |
| 18 | 3.84 | 1.0 | 6 | — | — | — | 4.71±0.81 | 25.6±2.9 | 6.50±1.5 |
| 26 | 3.84 | 1.0 | 6 | — | — | — | 4.46±0.75 | 14.6±1.4 | 3.94±1.0 |

It will be appreciated that the instant specification and examples are set forth by way of illustration and not limitation, and that various modifications and changes may be made without departing from the spirit and scope of the present invention.

What is claimed is:

1. A 12-epi-digoxin of the formula

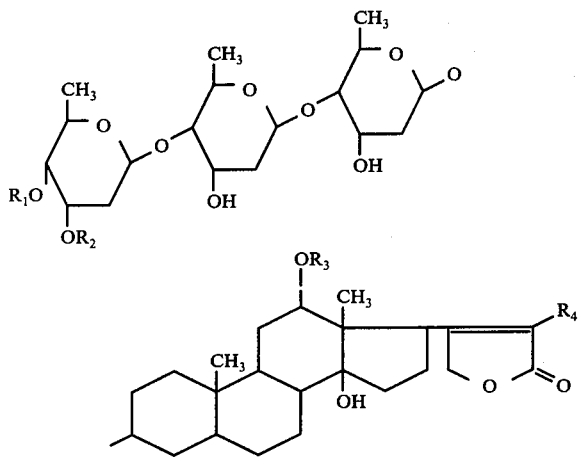

wherein $R_1$ and $R_2$ each independently is hydrogen, an acyl radical or a lower alkyl radical, $R_3$ is hydrogen or an acyl radical, and $R_4$ is hydrogen or an aliphatic hydrocarbon radical containing up to 4 carbon atoms.

2. A 12-epi-digoxin according to claim 1, wherein $R_1$ and $R_2$ each independently is hydrogen, an acyl radical containing up to 4 carbon atoms or an alkyl radical containing up to 4 carbon atoms, $R_3$ is hydrogen or an acyl radical containing up to 4 carbon atoms, and $R_4$ is hydrogen, or an alkyl, alkenyl or alkynyl radical containing up to 4 carbon atoms.

3. A 12-epi-digoxin according to claim 1, wherein said compound is 12-epi-β-methyldigoxin.

4. A 12-epi-digoxin according to claim 1, wherein said compound is 22-ethyl-12-epi-digoxin.

5. A 12-epi-digoxin according to claim 1, wherein said compound is 22-ethyl-12-epi-β-methyldigoxin.

6. A 12-epi-digoxin according to claim 1, wherein said compound is 12-acetyl-12epi-β-methyldigoxin.

7. A cardioactive composition of matter comprising a cardioactive effective amount of a compound according to claim 1 in admixture with a diluent.

8. A method of treating cardiac insufficiency in a patient which comprises administering to said patient a cardioactive effective amount of a compound according to claim 1.

9. The method of claim 8, wherein such compound is 12-epi-β-methyldigoxin, 22-ethyl-12-epi-digoxin, 22-ethyl-12-epi-β-methyldigoxin, or 12-acetyl-12-epi-β-methyldigoxin.

* * * * *